(12) United States Patent
Uchida et al.

(10) Patent No.: US 7,025,981 B2
(45) Date of Patent: Apr. 11, 2006

(54) THERAPEUTIC TOOL FOR VASCULAR DISEASES

(75) Inventors: Yasumi Uchida, 30-17, Narashinodai 2-chrome, Funabashi-shi, Chiba (JP) 274-0063; Haruko Uchida, Funabashi (JP)

(73) Assignee: Yasumi Uchida, Funabashi (JP)

( * ) Notice: Subject to any disclaimer, the term of this patent is extended or adjusted under 35 U.S.C. 154(b) by 327 days.

(21) Appl. No.: 10/237,012

(22) Filed: Sep. 9, 2002

(65) Prior Publication Data

US 2003/0053952 A1    Mar. 20, 2003

(30) Foreign Application Priority Data

Sep. 10, 2001    (JP) ............................. 2001-273832

(51) Int. Cl.
*A61F 2/02*    (2006.01)
(52) U.S. Cl. ..................................................... 424/423
(58) Field of Classification Search ................. 424/423
See application file for complete search history.

(56) References Cited

U.S. PATENT DOCUMENTS 5,073,071 A * 12/1991 Herwig et al. .............. 411/353
5,073,171 A    12/1991 Eaton
6,171,609 B1   1/2001 Kunz

OTHER PUBLICATIONS

C. Di Mario, "New recipes for in-stent restenosis: cut, grate, roast, of sandwich the neointima?" Heart 84:471-475, 2000.
Robert S. Schwartz, MD, "Pathophysiology of Restenosis: Interaction of Thrombosis, Hyperplasia, and/or Remodeling", Am J Cardiol 81 7A: 14E-17E, Apr. 9, 1998.
Donald Orlic et al, "Mobilized bone marrow cells repair the infarcted heart, improving function and survival", Proceedings of the National Academy of Sciences of the USA 98:10344-10349, Aug. 28, 2001.
Masataka Sata et al, "Circulating smooth muscle progenitor cells contribute to atherosclerosis", Nature Medicine 7: 382-383, Apr. 2001.

(Continued)

*Primary Examiner*—Carols A. Azpuru
(74) *Attorney, Agent, or Firm*—Oblon, Spivak, McClelland, Maier & Neustadt, P.C.

(57) ABSTRACT

The present invention relates to a therapeutic tool for vascular diseases, which is coated with a dye-containing resin that comprises one or more biocompatible dyes selected from the group consisting of sulfonic acid azo dye, phthalein dye, triphenylmethane dye, phenantridium dye, acrydine dye, xanthene dye, phenothiazine dye and cyanine dye; a medical treatment by the use of the therapeutic tool for vascular diseases; and a method of preventing vascular restenosis caused mainly through inhibition of migration of vascular progenitor cells by administering the medical treatment to a subject.

Since the present therapeutic tool for vascular diseases is capable of staying in vivo for a long term, a medical treatment such as angioplasty (coronary angioplasty, peripheral angioplasty, cerebral angioplasty, etc.) and blood vessel bypass (coronary bypass, peripheral bypass) by the use of the present tool can effectively inhibit the generation of blood vessel restenosis by inhibiting migration of vascular progenitor cells. Thus, the present tool is extremely useful in clinical situations.

20 Claims, 6 Drawing Sheets

OTHER PUBLICATIONS

Koichi Shimizu et al, "Host bone-marrow cells are a source of donor intimal smooth-muscle-like cells in murine aortic transplant arteriopathy", Nature Medicine vol. 7: 738-741, Jun. 2001.

Yasumi Uchida et al, "Participation of circulating smooth muscle-like cells (cSMLCs) in coronary restenosis after intervention", Circulation Journal 66 (Supplement I): 273, Apr. 2002.

Masataka Sata et al, "Hematopoietic stem cells differentiate into vascular cells that participate in the pathogenesis of atherosclerosis", Nature Medicine, vol. 8, 403-409, Apr. 2002.

* cited by examiner

THERAPEUTIC TOOL FOR VASCULAR DISEASES

TECHNICAL FIELD

The present invention relates to a therapeutic tool capable of effectively prevent vascular restenosis.

Also, the present invention provides methods for preventing vascular restenosis of various categories by inhibiting migration of vascular progenitor cells which are circulating in the blood into the blood vessel wall. In a preferred embodiment, the compound is selected from clinically applicable dyes such as Evans blue (blue dye), Ethidium bromide (fluorescent dye) and their analogues, and combination of one of them. A delivery system of them is selected from compound eluting stent, compound eluting graft and compound eluting stent-graft.

BACKGROUND ART

Restenosis is one of the serious complications of vascular interventions. such as balloon angioplasty, laser angioplasty, atherectomy and stenting. It also occurs after bypass grafting using autologous vessels or artificial grafts. Despite the use of drugs which inhibit platelet aggregation, thrombosis, smooth muscle proliferation, and/or immuno-suppresive and anti-cancer agents, restenosis occurs in 10–40% of patients who underwent vascular interventions or grafting. However, there are no clinically available compounds or tools which can completely prevent restenosis (Di Mario C: Heart 84: 471–475, 2000).

It has been generally believed that vascular smooth muscle cells (SMCs) pre-existing in the media migrate into the intima, proliferate excessively and differentiate into collagen fibers with subsequent production of abundant extracellular matrix, resulting in intimal hyperplasia and accordingly in restenosis (Schwartz R S: Am J Cardiol 81: 14E–17E, 1998).

Recently, however, it was demonstrated that bone marrow-derived vascular progenitor cells migrate into the intima from vascular lumen and cause intimal hyperplasia of mechanically injured animal vessels (Orlic D, et al: Proc Natl Acad Sci USA 98: 10344–10349, 2001; Sata M et al: Nature Science 8: 403–409, 2002.). Also, the progenitor cells participate in restenosis at the site of implanted artificial grafts and aortic transplant arteriopathy (Shimizu K: Nature Science 7: 738–741, 2001).

DISCLOSURE OF THE INVENTION

The present inventors found that circulating vascular progenitor cells are positive not only to factors such as $CD_{34}$, GFAP, factor 8 and vimentin but also to beta-smooth muscle actin, indicating that they have potentials to differenciate into endothelial cells, smooth muscle cells, fibroblasts and glial cells and that they migrate through the walls of vasa vasolum, such as capillaries, arterioles and venules into the interstitial space of the adventitia of injured vessels. The present inventors also found that in mechanically damaged arteries they migrate into the intima by three routs, namely 1) from adventitia traversing and destructing the media, 2) directly from the lumen and 3) from newly formed vessels in the hypertrophic neointima, and proliferate producing extracellular matrix, and their migration from adventitia into the intima plays the major role in intimal hyperplasia and resultant restenosis (Uchida Y et al: Circulation J 66 (Suppl I): 273, 2002).

Therefore, it was undertaken to find out the compounds which effectively prevent migration of the circulating progenitor cells into the vessel wall and to develop clinically applicable tools by which the compounds can be locally delivered.

BRIEF DESCRIPTION OF THE DRAWINGS

FIG. 2 shows schematic representation of dye-coated stents. A: longer axis configuration of the stent. B: shorter axis configuration of a stent strut. C: a strut with circular grooves. D: a strut with spiral grooves. 1: a strut. 2: rapidly eluting dye layer. 3: gradually eluting dye layer. 4: strut core. 6: circular prominence. 7: spiral prominence.

FIG. 6 shows angioscopic and histologic appearances of the stented coronary segments. A (upper left): angioscopically identified severe stenosis of a coronary segment 4 weeks after implantation of a Palmatz-Schatz stent without coated with Evans blue. B (upper right): angioscopically identified no obvious stenosis in a coronary segment implanted with a Evans blue coated Palmatz-Schatz stent. C (lower left) and D (lower right): fluorescent microscopic appearances of the coronary segments showing collagen deposition. Fluorescence of collagen was excited by 360 nm and collected by 430 nm. C and D correspond to A and B, respectively. ×40. Arrows: stent strut. Arrow heads: intima. L indicates coronary lumen.

BEST MODE FOR CARRYING OUT THE INVENTION (a) Dyes and Dye-Containing Resins

The biocompatible dye used in the therapeutic tool for vascular diseases of the present invention is a dye that has been used as a dye for a medical use such as a dye for medicine, living body or biomaterials, and a dye for use in foods, which biocompatible dye can be administered in mammal, including a human, and which is selected from sulfonic azo dye, phthalein dye, triphenylmethane dye, phenanthridinium dye, acridine dye, xanthene dye, phenothiazine dye or cyanine dye.

The sulfonic azo dye used herein may be an azo dye having a group $-SO_3^-$, the examples thereof including a naphthalene sulfonic azo dye, such as Evans Blue, Trypan Blue, Trypan Red, and Orange B; Polar Yellow, Orange I and Orange II. The examples of the phthalein dye include phenolphthalein and phenolsulfophthalein. The examples of the triphenylmethane dye include Gentian Violet and Fuchsin (Majenta). The examples of the phenanthridinium dye include Ethidium bromide, Ethidium chloride and Propidium iodide. The examples of the acridine dye include Acridine Orange, Acridine yellow, 9-aminoacridine, Acriflavin, and Proflavin. The examples of the xanthene dye include Rhodamine B, Sulforhodamine, Fluorescein and Eosine. The examples of the phenothiazine dye include Methylene blue, Toluidine blue and Azur (A, B).

Among them, preferred are naphthalene sulfonic azo dyes such as Evans Blue, Trypan Blue, Trypan Red and Orange B; and phenanthridinium dyes such as ethidium bromide and propidium iodide, with Evans Blue and ethidium bromide being especially preferred.

Such dyes exhibit an action of inhibiting adherence and invasion of smooth muscle cells (vascular progenitor cells) into a site enlarged by a balloon of dog's coronary artery.

Evans blue and its derivatives are the compounds which effectively inhibit migration of circulating vascular progenitor cells into the vessel wall after angioplasty in animals.

Evans blue and its derivatives are the compounds which prevent vascular restenosis after angioplasty in animals and man.

Ethidium bromide (Homijium) and its derivatives are the compounds which prevent migration of circulating vascular progenitor cells into the vessel wall after angioplasty in animals.

Ethidium bromide (Homijium) and its derivatives are the compound which prevent vascular restenosis after angioplasty in animals.

Evans blue and Ethidium bromide and their derivatives are the compounds which prevent coronary restenosis induced by angioplasty (balloon angioplasty, stent implantation, cutting balloon angioplasty, laser angioplasty, directional angioplasty, etc) and bypass grafting in patients.

Other dyes such as sulfonic acid azo-dyes, phthalein dyes, triphenylmethane dyes, phenantholijium dyes, acrizine dyes, xanthine dyes, phenotiazine dyes and cyanide dyes which are clinically applicable.

Thus, an angioplasty that uses the present therapeutic tool for vascular diseases coated by the dye-containing resin can effectively prevent the applied site from adherence and invasion of progenitor cells to applied sites, thereby effectively preventing vascular restenosis.

The dye-containing resin of the present invention is prepared by mixing the above-recited dyes and a resin. Such resins are not limited, provided that they have extensibility, flexibility and moisture-permeability, which are properties suitable for film formation, and display no drawback when applied in vivo. The examples thereof include polyolefins such as polyethylene, polypropylene, polybutene, SEBS, SIS, polyolefin copolymers; acrylic resin such as polymethylmethacrylate; fluororesins such as polytetrafluoroethylene; thermoplastic resins such as polystyrene, polyvinyl chloride, polyurethane, polyamide, polyester, cellulose, polycarbonate, nylon, silicone, and natural rubber latex.

(b) Invented Tools for Local Administrations

The therapeutic tool for vascular diseases of the present invention is prepared by coating the surface of a therapeutic tool that is used generally in angioplasty with the above-recited dye-containing resin. No limitations are imposed on the shape and material of the therapeutic tool except that it is for use in a therapy of blood vessel, and can be retained in blood vessel. Such a material may be either biodegradable (autoabsorbable and autolyseable) or bionondegradable, and is exemplified by metals or ceramics such as stainless steel, nickel-titanium alloy, and tantalum; nonbiodegradable materials such as polyethylene tetrafluoride, polyethylene trifluoride, polyethylene, polyethylene telephthalate, and polypropylene; and biodegradable materials such as polylactic acid, polyglicolic acid, and poly α-amino acid.

No limitations are imposed on the shape of the tool, provided that it is strong enough for stably staying on the inner wall of blood vessels, preferable examples thereof being a cylindrical shape formed by net. Specifically, preferred are stent, stentgraft, catheter, balloon, artificial graft, with the stent and artificial graft being particularly preferred. The shape of the stent may be coil, or net-cylinder, and may further be rigid or flexible stent.

The therapeutic tool for vascular diseases may be a stent, artificial graft, stent-graft or balloon. The internal diameter, external diameter and length of the stent are in the range from 0.05 mm to 5 cm, 1 mm to 5.4 cm, and 0.5 cm to 30 cm, respectively.

The therapeutic tool for vascular diseases may be an artificial graft whose internal diameter, external diameter and length are in the range of from 0.1 mm to 5 cm, from 0.2 mm to 5.5 cm, and from 5 mm to 50 cm, respectively.

The therapeutic tool for vascular diseases may be a stent-graft whose internal diameter, external diameter and length are in the range from 0.5 mm to 5 cm, from 0.7 mm to 5.5 cm, and from 0.5 cm to 50 cm, respectively.

Stents covered with one or more of the compounds listed in (a) enable rapid and gradual elution of the compounds into the vascular wall. Artificial grafts and stent-grafts covered with one or more of the compounds listed in (a) enable rapid and gradual elution of the compounds into the vascular wall.

Coating of the dye-containing resin onto said therapeutic tool may be carried out by dissolving a resin into an organic solvent, including ordinary alcohols, ethers such as dioxane, aprotic polar solvent such as dimethylformaldehyde, dimethylsulfoxide; mixing a dye therein; dissolving the dye at room temperature or under heat if necessary to produce a dye-containing resin solution; dipping the therapeutic tool in the solution or spraying it on the tool; followed by drying and fertilizing. In order for the dye to release immediately after the insertion of the therapeutic tool and continue to relieve over a long time, it is preferred that following the coating, a further coating of a solution of a dye or a polymer (gelatin, hydroxypropylmethylcellulose, etc) that contains the dye be made to obtain a multilayer coating. For example, a release-continuing layer may be first formed by coating the tool with a dye-containing resin solution using urethane resin, and then an abrupt release layer may be formed by coating the firstly coated layer with hydroxypropylmethylcellulose containing a dye or gelatin solution.

The dye content in the dye-containing resin solution is preferably 1–50%, suitably 1–25%, and especially 10–20%, in terms of restenosis prevention.

By the use of the thus obtained therapeutic tool for vascular diseases of the present invention, restenosis caused by interventional and surgical therapies of atherosclerotic, thrombotic and inflammatory obstruction of coronary, cerebral, pulmonary, peripheral, abdominal vessels, and large vessels such as aorta and caval veins, can effectively be prevented.

EXAMPLES

Example 1

Demonstration of Migration of Vascular Progenitor Cells into the Injured Coronary Arterial Wall and Its Prevention by Local Delivery of Dyes

Materials and Methods

Adult beagle dogs of either sexes weighing from 7 to 12 kg were anesthetized with pentobarbital sodium (25–30 mg/kg, i.v.) and the trachea was intubated for artificial respiration with air. The right side of the neck was longitudinally incised to expose the right common carotid artery and an 8 F sheath was introduced, through which an 8F guiding catheter was introduced into the left coronary ostium for angiography. After angiography, a balloon catheter (2.5 mm×20 mm) was introduced through the guiding catheter into the middle to distal segment of either the anterior descending or circumflex artery. Then, the balloon was inflated at 9 atms to dilate the segment to induced disruption of the endothelium and internal elastic lamina. The balloon catheter was replaced by a porous balloon catheter (3 mm×20 mm) with multiple pores in the balloon (Clinical Supply Co, Gifu, Japan) for local delivery of dyes. Thereafter, 0.2 ml of 5% Evans blue saline solution was injected through the porous balloon into the dilated segment at 3 atms in 6 dogs and 0.5 ml of 5% Ethidium bromide saline solution was injected similarly in 5 dogs. In other 6 dogs, 0.5 ml saline alone was injected as the control group. The porous balloon and sheath were then removed and the incised wound was closed. After recovery from anesthesia, the dogs were cared according to the guideline of our university (Jikei University School of Medicine) ethical committee. One week later, the dogs were anesthetized again and coronary angiography was repeated. Then, the heart was arrested with intracoronary pentobarbital sodium and the heart was removed. The heart was fixed with 10% hormaldehyde. The dilated coronary segment and its surrounding tissues were removed and sliced, vascular progenitor cells were stained with beta-smooth muscle actin antibody (DAKO EPOS, Glostrup, Denmark) and the number of vascular progenitor cells/250×250 $\mu m^2$ was counted.

Results

In FIG. 1, A, B and C show a circulating vascular progenitor cell in the coronary artery, those attached on the coronary luminal surface and those migrated into the coronary wall of control dogs, respectively. In contrast, no migration of the cells was observed in the coronary wall treated with Evans blue as shown in D.

As shown in Table I, the number of vascular progenitor cells/unit area was significantly smaller in the dogs treated with Evans blue or Ethidium bromide.

TABLE I

Effects of Local Delivery of Evans Blue and Ethidium Bromide on Migration of Vascular Progenitor Cells into the Coronary Arterial Wall

|  | Number of dogs | Number of cells (250 × 250 $\mu m^2$) |
| --- | --- | --- |
| Control group | 6 | 7.3 ± 1.3 |
| Evans blue group | 6 | 0.8 ± 0.3** |
| Ethidium bromide | 5 | 0.4 ± 0.1** |

**$P < 0.01$ vs control group.

Conclusion

The results indicate that both Evans blue and Ethidium bromide inhibit migration of circulating vascular progenitor cells into the injured coronary wall in dogs.

Example 2

Production of Dye-Coated Tools for Treatment of Vascular Diseases

1. Dye-Eluting Stents a) A soft polycarbonate urethane with risin bionate (Bionate 80A, Polimertech, USA) was used. Evans blue powder was dissolved in the bionate to make 20% Evans blue solution. A commercially available coronary stent (NIR stent, 3 mm×12 mm or Palmatz-Schatz stent, 3 mm×12 mm) was immersed into the solution for 10 min to form slowly eluting inner layer. Then, the stent was dried at room temperature. Evans blue powder was dissolved in distilled water to make 20% solution. The same stent was immersed into the solution for 10 min to make rapidly eluting outer layer. The stent was dried at room temperature. Then, the stent was sterilized with ethylene oxide gas. In the preliminary experiment in vitro, Evans blue began to elute from the outer layer immediately after and ceased to elute within 60 min after immersion into water. Evans blue began to elute from the inner layer 60 min after immersion into water and continued to elute for up to one month.

Figure 1A:
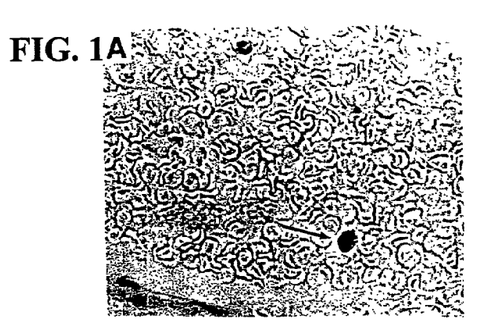
FIG. 1 shows migration of vascular progenitor cells (identified by beta-smooth muscle actin stain) from lumen into the mechanically injured coronary arterial wall of beagle dog and its prevention with local administration of Evans blue. A (upper left): a circulating vascular progenitor cell (arrow). B (upper right): progenitor cells migrating into an injured coronary segment (arrows). C (lower left): progenitor cells migrated into the intima (arrows). D (lower right): a coronary segment treated with Evans blue. A and B: 2 weeks after balloon angioplasty. C: 4 weeks after balloon angioplasty D: 4 weeks after balloon angioplasty and local delivery of 2% Evans blue solution by a porous balloon.
Figure 1B:
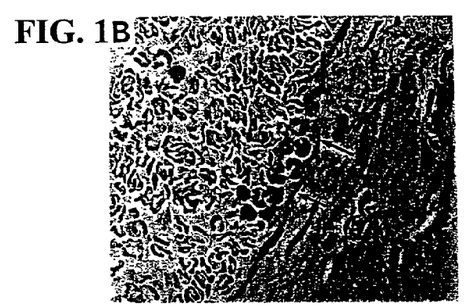
Figure 1C:
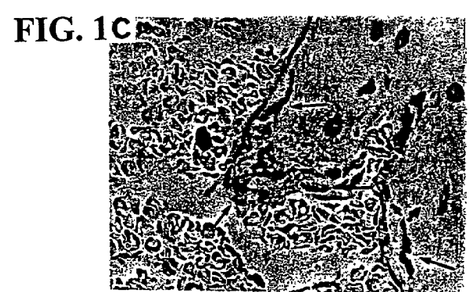
Figure 1D:
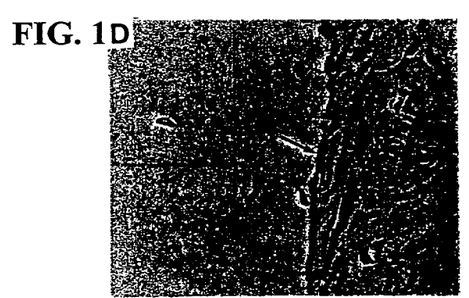
Figure 2A:
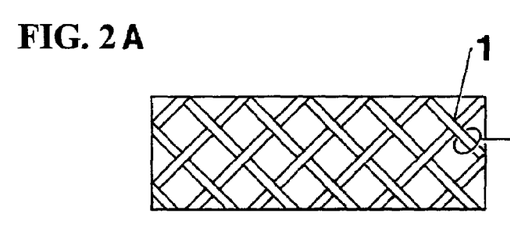
Figure 2B:
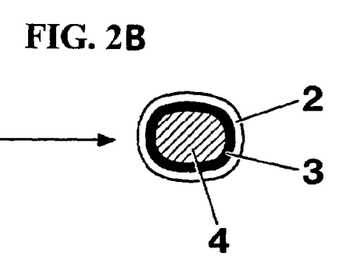
Figure 2C:
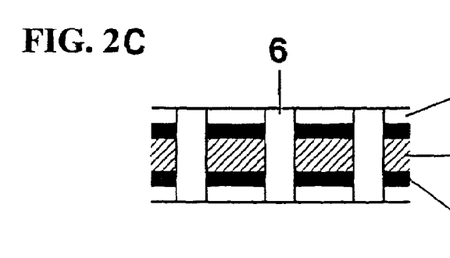
Figure 2D:
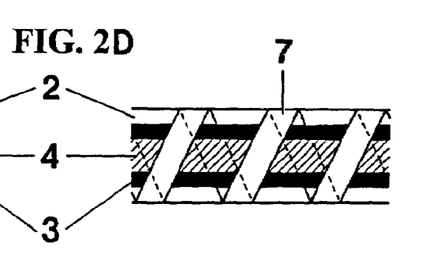
Figure 3A:
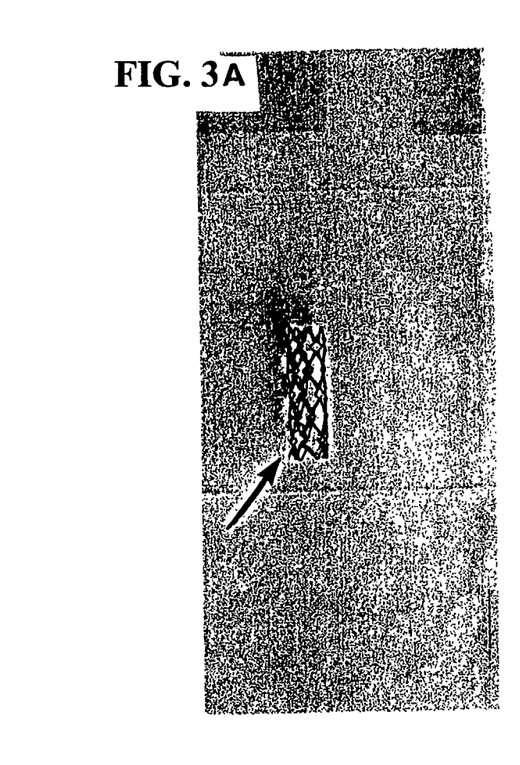
FIG. 3 shows a commercially available stent (NIR stent) coated with Evans blue. A (left): the stent in expanded state (arrow). B (middle): the stent in the distilled water showing rapid elution of Evans blue. 1: stent. 2: eluted Evans blue. C (right): the stent mounted on a balloon catheter. 1: stent. 2: balloon catheter for coronary angioplasty.
Figure 3B:
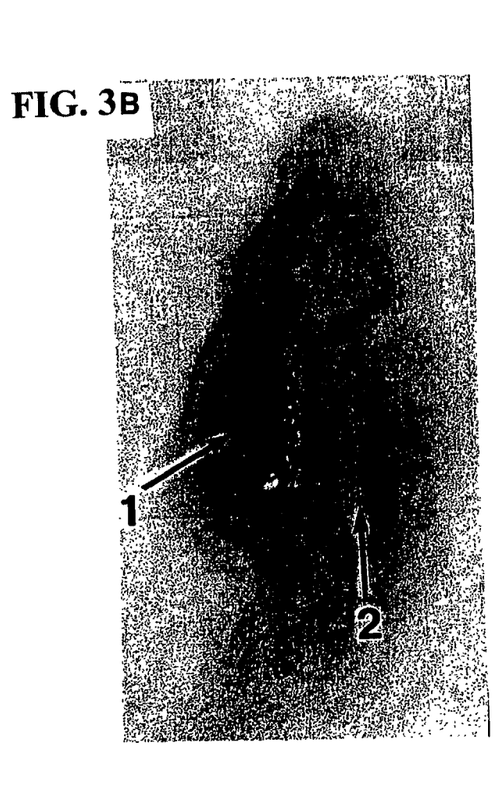
Figure 3C:
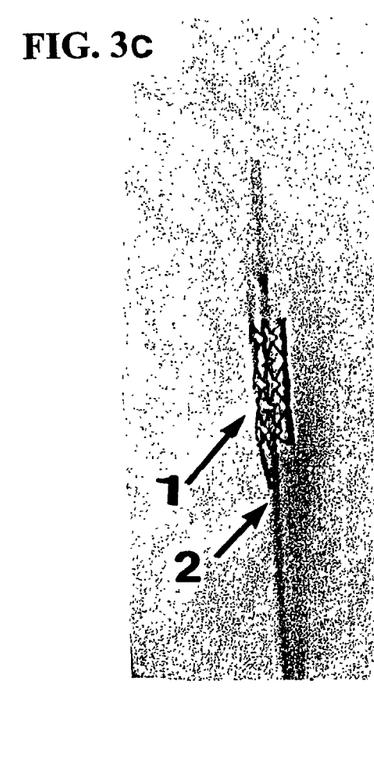

Similarly, a stent was immersed into 10% Ethidium bromide bionate solution and then into 10% Ethidium bromide water solution to make a double dye-layered stent.

b) An expandable, flexible and water-permeable urethane resin with Sanpren LQ-336N (Sanyo Chem Co, Tokyo, Japan) was mixed with DMF to make 30% resin solution. Either Evans blue powder or Ethidium bromide powder was added to the solution so as to make 20% Evans blue solution or 10% Ethidium bromide solution. Then, a coronary stent described above, was immersed into the solution to make a slowly eluting layer (inner layer). Thereafter, stent was dried and then immersed into 20% Evans blue water solution to make a rapidly eluting layer (outer layer). Thereafter the stent was sterilized similarly.

c) FIG. 2 shows schematic representation of dye-eluting stent thus made. In order to mount the dyes in larger amount and to prevent exfoliation of the dye layers during expansion of the stent, the stent strut should have circular or spiral grooves as shown in C and D of the figure. FIG. 3 shows a NIR stent covered with double layers of Evans blue. From left to right panel, the stent in expanded state, rapidly eluting Evans blue from the strut in water and the stent mounted on a balloon catheter, respectively.

2. Dye-Eluting Artificial Grafts

A commercially available artificial graft with Regular Graft (Goatex EPTFE 4 mm, W. L. GORE & ASSOCIATES INC, Flagstaff, USA) was used. The graft was cut into 5 cm in length. The entire luminal surface and outer surface of both cut ends 5 mm in length were coated with above-described bionate or Sanpren solution of either Evans blue or Ethidium bromide to make slowly eluting layer (inner layer). After drying, the surfaces were again coated with aqueous solution of either of these dyes to make rapidly eluting layer (outer layer). Thereafter, the graft was sterilized with ethylene oxide gas and was stored until use.

Figure 4:
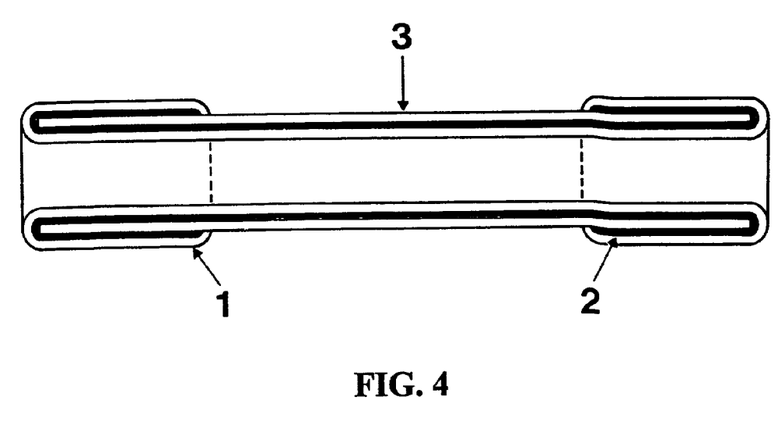
FIG. 4 shows schematic representation of dye-coated artificial graft. 1: rapidly eluting layer. 2: gradually eluting layer. 3: artificial graft.
Figure 5:
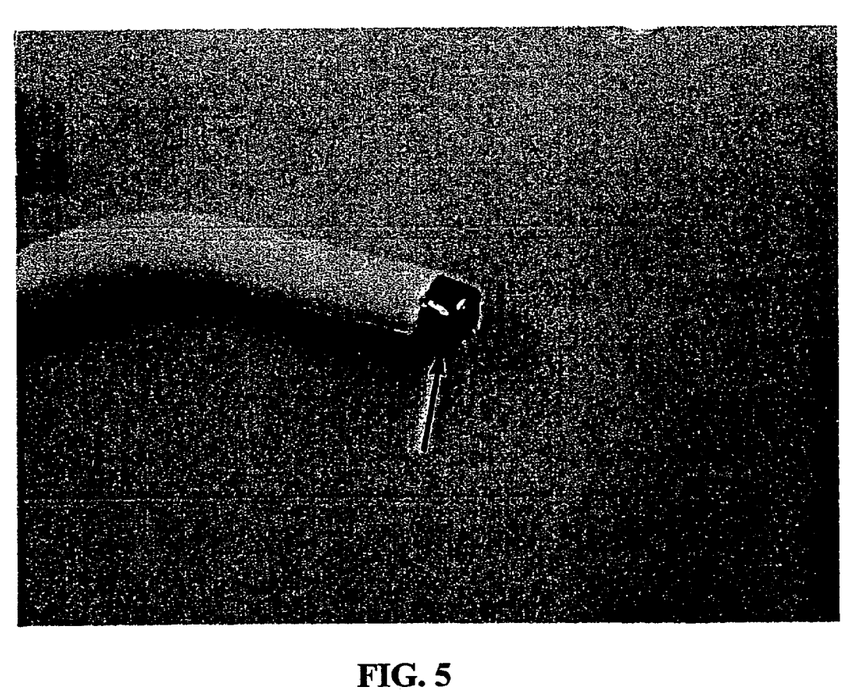
FIG. 5 shows an artificial graft (Goatex EPTFE II, 4 mm; W.L. GORE & ASSOCIATES INC, Flagstaff, USA) coated with Evans blue. Arrow: Evans blue layer.
Figure 6A:
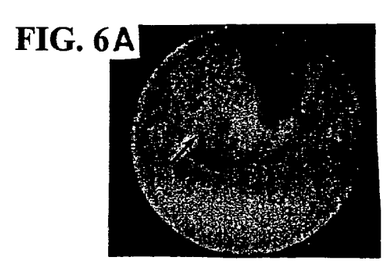
Figure 6B:
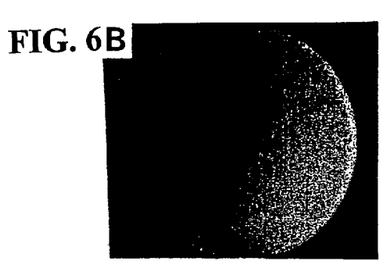
Figure 6C:
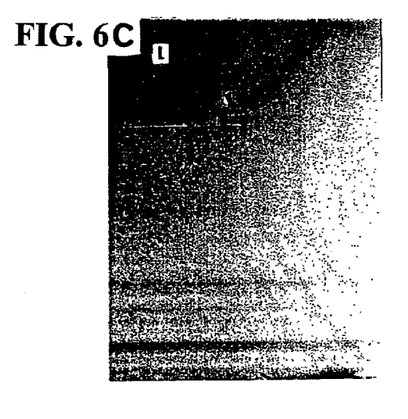
Figure 6D:
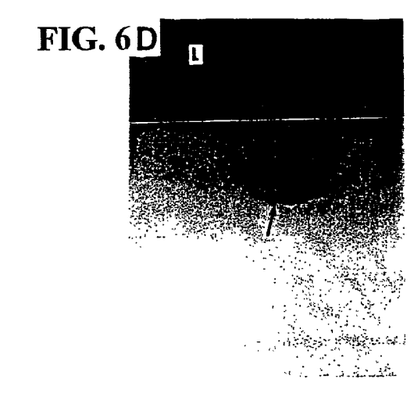

FIG. 4 shows schematic representation of the dye-coated artificial graft and FIG. 5 shows an artificial graft double coated with Evans blue.

Example 3

Implantation of Dye-Eluting Stents into Canine Coronary Artery

Materials and Methods

Beagle dogs of either sex was anesthetized with pentobarbital sodium (25 mg/kg, i.v.) and trachea was intubated for artificial respiration with air. The right side of the neck was incised longitudinally to expose right common carotid artery. An 8F sheath was introduced into the artery through which an 8F guiding catheter was introduced into the left coronary artery. After coronary angiography, a balloon catheter clinically used for PTCA was introduced to dilate anterior descending artery. Then, a balloon catheter with a dye-eluting stent on it was introduced into the dilated segment of left anterior descending artery and it was inflated at 9 atms to implant the stent. After recovery from anesthesia, the dogs were cared according the guideline of Jikei University School of Medicine. One month later, the dogs were anesthetized again and coronary angiography and angioscopy (Uchida Y: Coronary Angioscopy, Futura Publishing Co, NY, 2000) were performed to examine the changes in the stented coronary segment. In other group of dogs, the stent coated with bionate or Sanpren which did not contain dyes was implanted and this group of dogs was used as control. Thereafter, the dogs were sacrificed with intracoronary pentobarbital and the heart was removed. The heart was fixed with 10% hormaldehyde solution for microscopic examination.

The coronary angiograms were used for calibration of the percentage stenosis, namely (diameter before stent implantation−minimum luminal diameter/diameter before stent implantation)×100 of the narrowest portion (minimum luminal diameter) in the stent and was compared. Student's t test was used for statistical analysis and when $P<0.05$, the value was considered significant.

The stented coronary segment was removed and cut into slice in 5 μm in thickness. The slices were stained with beta-actin antibody and the number of vascular progenitor cells per unit area was counted and was compared between the dye and control groups.

Results

FIG. 6 shows angioscopic appearances of the interior of the stented coronary segments and their fluorescent microscopic changes. In control dogs, severe narrowing of stented coronary segment was observed as shown in panel A. On the other hand, in Evans blue group, stenosis was mild and the dye remained in the wall as shown in panel B. Collagen in the wall was excited by ultraviolet ray at 360 nm and collected at 460 nm. The intima of the control group was thick and occupied with collagen as shown in panel C while it was thin in dye-treated group as shown in panel D. Similar changes were observed in Ethidium group.

Figure 7:
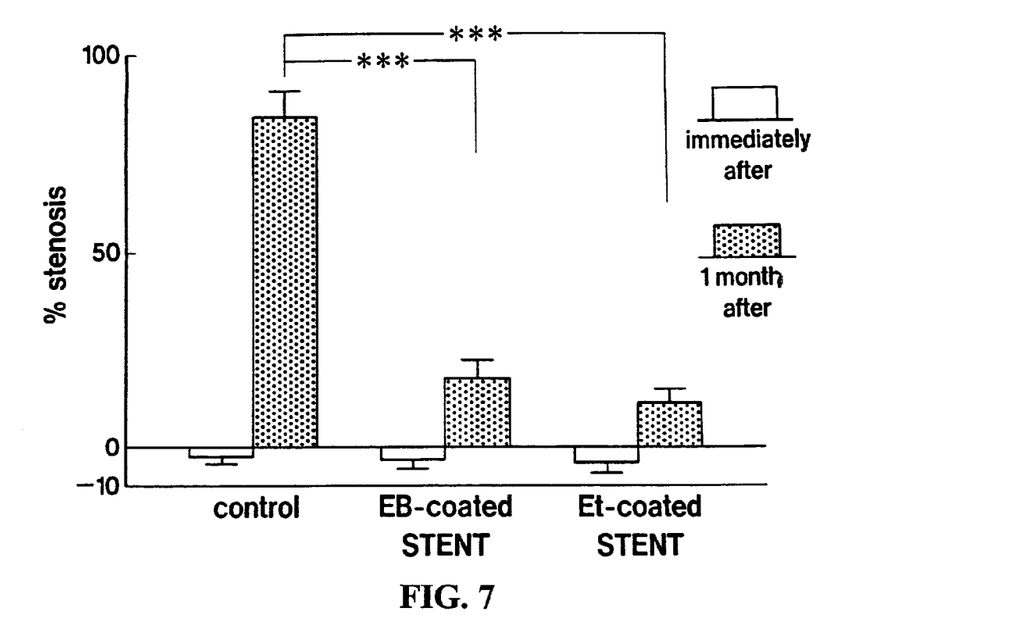
FIG. 7 shows percentage stenoses of the coronary artery of beagle dogs 4 weeks after implantation of stents coated with or without Evans blue or Ethidium bromide. EB: Evans blue. Et: Ethidium bromide

FIG. 7 shows percentage stenosis of the stented coronary segments. It was revealed that percentage stenosis was significantly smaller in Evans blue and Ethidium groups and percentage stenosis exceeding 50% was not observed in the dye groups.

Table II shows the results the number of progenitor cells in the intima, media and adventitia of the stented coronary segment.

TABLE II

Vascular Progenitor Cells in the Stented Coronary Artery

| | Number of dogs | Number of cells (250 × 250 μm$^2$) |
|---|---|---|
| Intima | | |
| Control group | 6 | 37.8 ± 7.7 |
| Evans blue group | 6 | 7.1 ± 3.2** |
| Ethidium group | 6 | 8.3 ± 3.7** |
| Media | | |
| Control group | 6 | 22.2 ± 7.0 |
| Evans blue group | 6 | 8.0 ± 4.0* |
| Ethidium group | 6 | 9.6 ± 5.0* |
| Adventitia | | |
| Control group | 6 | 40.2 ± 11.0 |
| Evans blue group | 6 | 17.0 ± 7.1* |
| Ethidium group | 6 | 21.3 ± 9.9* |

*$P < 0.05$,
**$P < 0.01$, vs control.

Conclusion

The results indicate that coronary restenosis and migration of vascular progenitor cells into the coronary artery are inhibited by dye-eluting stents.

Example 4

Grafting of Dye-Eluting Artificial Grafts to Canine Common Carotid Artery

Materials and Methods

In anesthetized beagle dogs, the bilateral sides of the neck were incised to expose both right and left common carotid arteries. An 8 F sheath was introduced into the right femoral artery through which a 8 F catheter was introduced into the aortic arch for angiography of the carotid arteries. A dye-eluting artificial graft was sutured to the common carotid arteries in side to end fashion to make a shunt between the right and left common carotid arteries. Then, a segment of right carotid artery proximal to and that of left distal to anastomoses were ligatured. Thus, the blood drained from the left to the right common carotid artery. Similarly in other group, grafts coated with bionate or Sanpren without dye were sutured to the arteries as control group. The dogs were cared for 3 months according to the guideline and angiography was repeated. Percentage stenosis of the sutured portion was compared between the dye and control groups. After cardiac arrest as mentioned above, the grafts and arteries were removed and were used for microscopic examinations.

Results

Figure 8:
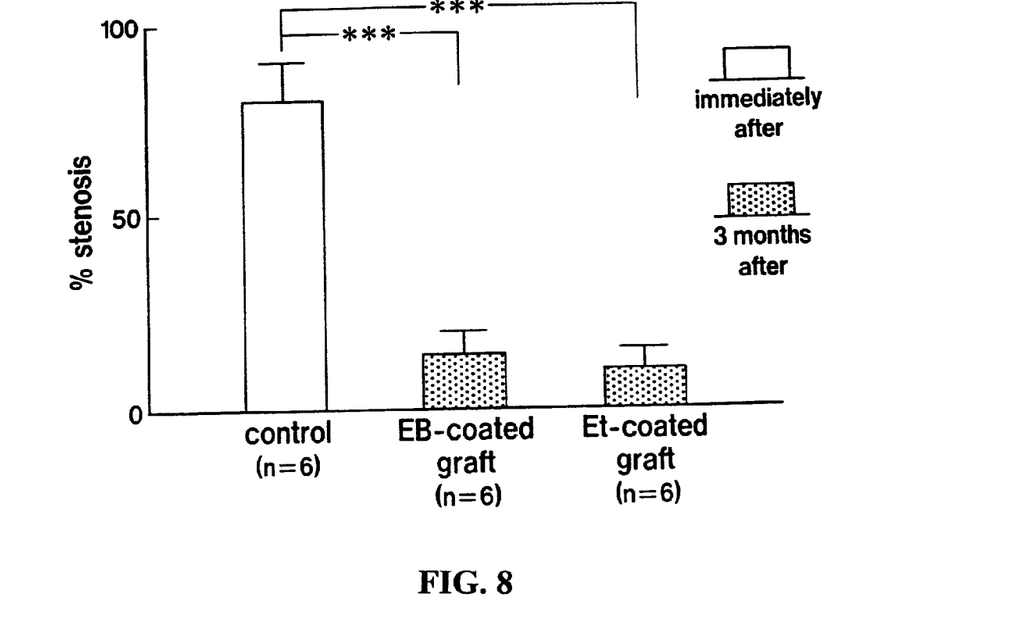
FIG. 8 shows percentage stenoses of the common carotid artery of beagle dogs 3 months after grafting of the artificial grafts coated with or without Evans blue or Ethidium bromide.

FIG. 8 shows percentage of stenosis at the sutured portion. Percentage stenosis was significantly smaller in dye groups. Also, number of vascular progenitor cells per unit area was significantly smaller in the dye groups (Table III).

TABLE III

Vascular Progenitor Cells at the Anastomosed Portion of the Common Carotid Artery

| | Number of dogs | Number of cells (250 × 250 μm$^2$) |
|---|---|---|
| Control group | 6 | 27.9 ± 6.0 |
| Evans blue group | 6 | 13.4 ± 4.0* |
| Ethidium group | 6 | 11.1 ± 3.1* |

INDUSTRIAL APPLICABILITY

These novel dye-coated tools for therapy of vascular diseases are implantable into the human body and can be left in the body for long time. Clinically, they are very useful for prevention of restenosis mainly caused by migration of vascular progenitor cells and which frequently occur after recanalization of obstructed vessels such as angioplasty of coronary, peripheral and cerebral vessels and bypass surgery of these vessels.

What is claimed is:

1. A therapeutic tool for vascular diseases, which is coated with a dye-containing resin that comprises one or more biocompatible dyes selected from the group consisting of a sulfonic acid azo dye, phthalein dye, triphenylmethane dye, phenantridium dye, acrydine dye, xanthene dye, phenothiazine dye and cyanine dye, or
 a specific dye selected from the group consisting of at least one of Trypan Blue, Trypan Red, Orange B, propidium iodide, Evans Blue and ethidium bromide, wherein the dye content of the dye-containing resin is in the range of 1–50%.

2. The therapeutic tool for vascular diseases of claim 1 which is a stent, artificial graft, stent-graft or balloon.

3. A therapeutic tool for vascular diseases, which is coated with a dye-containing resin that comprises one or more biocompatible dyes selected from the group consisting of sulfonic acid azo dye, phthalein dye, triphenylmethane dye, phenantridium dye, acrydine dye, xanthene dye, phenothiazine dye and cyanine dye, which is:
 a stent whose internal diameter, external diameter and length are in the range from 0.05 mm to 5 cm, 1 mm to 5.4 cm, and 0.5 cm to 30 cm, respectively,
 an artificial graft whose internal diameter, external diameter and length are in the range of from 0.1 mm to 5 cm, from 0.2mm to 5.5 cm, and from 5mm to 50cm, respectively, or
 a stent-graft whose internal diameter, external diameter and length are in the range from 0.5 mm to 5 cm, from 0.7 mm to 5.5 cm, and from 0.5 cm to 50 cm, respectively.

4. The therapeutic tool for vascular diseases of claim 3, which is a stent composed of stent struts coated with at least one dye-containing substances.

5. The therapeutic tool for vascular diseases of claim 4, wherein the strut is composed of a mixture of resin and one of more of dyes the concentration of which is in the range from 1 to 25%, the strut being optionally autolyseable and autoabsorbable.

6. The therapeutic tool for vascular diseases of claim 3, which is an artificial graft whose internal diameter, external diameter and length are in the range of from 0.1 mm to 5 cm, from 0.2mm to 5.5 cm, and from 5 mm to 50cm, respectively.

7. The therapeutic tool for vascular diseases of claim 6, wherein the artificial graft is composed of the mixture of resin and one or more of the dyes the concentration of which is in the range from 1 to 50%, the artificial graft being optionally autoabsorbable and autolyseable.

8. The therapeutic tool for vascular diseases of claim 3, which is a stent-graft whose internal diameter, external diameter and length are in the range from 0.5 mm to 5 cm, from 0.7 mm to 5.5 cm, and from 0.5 cm to 50 cm, respectively.

9. The therapeutic tool for vascular diseases of claim 8, wherein the stent-graft is composed of artificial graft of any kind and stent strut, both of which are coated with dye-containing resin, the concentration of the dye being in the range from 1 to 50%, and both of the artificial graft and the stent strut being optionally autolyseable and autoabsorbable.

10. A method for treating vascular restenosis comprising:
 administering to a subject in need thereof a medical treatment that uses a therapeutic tool for vascular diseases that comprises one or more biocompatible dyes selected from the group consisting of sulfonic azo dye, phthalein dye, triphenylmethane dye, phenantridium dye, acrydine dye, xanthene dye, phenothiazine dye and cyanine dye.

11. The therapeutic tool for vascular diseases of claim 1, wherein the dye content ranges from 1–25%.

12. The therapeutic tool for vascular diseases of claim 1, wherein the dye content ranges from 10–20%.

13. The therapeutic tool for vascular diseases of claim 1, wherein the dye-containing resin coating is coated with a second coating comprising a solution of a dye, or a polymer that contains a dye.

14. The therapeutic tool for vascular diseases of claim 13, wherein said dye-containing coating is formulated as a continued-release layer and said second coating is formulated as an abrupt release layer.

15. The therapeutic tool for vascular diseases of claim 13, wherein said second coating comprises a dye in combination with at least one polymer selected from the group consisting of gelatin and hydroxypropylmethylcellulose.

16. A method for treating vascular restenosis comprising administering to a subject in need thereof, or treating a subject in need thereof with, the therapeutic tool of claim 1.

17. The method of claim 16, wherein said vascular restenosis is caused by interventional and surgical therapy of atherosclerotic, thrombotic, or inflammatory obstruction of coronary, cerebral, pulmonary, peripheral, or abdominal vessels.

18. The therapeutic tool for vascular diseases of claim 1, wherein the dye is selected from the group consisting of at least one of Trypan Blue, Trypan Red, Orange B, and propidium iodide.

19. The therapeutic tool for vascular diseases of claim 1, wherein the dye comprises Evans Blue.

20. The therapeutic tool for vascular diseases of claim 1, wherein the dye comprises ethidium bromide.

* * * * *